United States Patent
Akui

(10) Patent No.: US 12,390,093 B2
(45) Date of Patent: Aug. 19, 2025

(54) ENDOSCOPE, BENDING OPERATION MECHANISM FOR ENDOSCOPE, AND OPERATION PORTION FOR ENDOSCOPE

(71) Applicant: OLYMPUS CORPORATION, Tokyo (JP)

(72) Inventor: Nobuaki Akui, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 517 days.

(21) Appl. No.: 17/725,817

(22) Filed: Apr. 21, 2022

(65) Prior Publication Data
US 2022/0240754 A1 Aug. 4, 2022

Related U.S. Application Data

(63) Continuation of application No. PCT/JP2019/042142, filed on Oct. 28, 2019.

(51) Int. Cl.
*A61B 1/005* (2006.01)
*A61B 1/00* (2006.01)

(52) U.S. Cl.
CPC ........ *A61B 1/0052* (2013.01); *A61B 1/00114* (2013.01); *A61B 1/0057* (2013.01)

(58) Field of Classification Search
CPC .............. A61B 1/0052; A61B 1/00066; A61B 2017/003; A61B 2017/00318; A61B 34/74; A61B 2034/741–744; A61B 1/00039; A61B 1/00042; A61B 1/005; A61B 1/0051; A61B 1/0057; A61M 25/0136; A61M 25/0133; A61M 25/0147
USPC ........................................ 600/131, 146, 149
See application file for complete search history.

(56) References Cited

U.S. PATENT DOCUMENTS

| | | | | |
|---|---|---|---|---|
| 2011/0144576 A1* | 6/2011 | Rothe | ............... | A61M 25/0136 604/95.04 |
| 2012/0302832 A1* | 11/2012 | Inada | ................... | A61B 1/0052 600/118 |
| 2019/0029498 A1 | 1/2019 | Mankowski et al. | | |

FOREIGN PATENT DOCUMENTS

| | | | |
|---|---|---|---|
| EP | 0077526 A2 | * | 4/1983 |
| EP | 3434169 A1 | | 1/2019 |
| JP | 2012100683 A | | 5/2012 |
| JP | 2016055041 A | | 4/2016 |
| WO | WO-2017145431 A1 | * | 8/2017 |

OTHER PUBLICATIONS

International Search Report dated Dec. 24, 2019 issued in PCT/JP2019/042142.

* cited by examiner

*Primary Examiner* — Michael J Carey
*Assistant Examiner* — Timothy Tuan Luu
(74) *Attorney, Agent, or Firm* — Scully, Scott, Murphy & Presser, P.C.

(57) ABSTRACT

An endoscope includes: a first bearing including a first recess along a first central axis; a second bearing disposed in the first recess and provided with a second central axis intersecting the first central axis in the state of being disposed in the first recess, the second bearing including a second recess along the second central axis and being retained turnably around the first central axis; and an operation lever disposed in the second recess, and including a shaft member retained turnably around the second central axis.

19 Claims, 14 Drawing Sheets

ENDOSCOPE, BENDING OPERATION MECHANISM FOR ENDOSCOPE, AND OPERATION PORTION FOR ENDOSCOPE

CROSS REFERENCE TO RELATED APPLICATION

This application is a continuation application of PCT/JP2019/042142 filed on Oct. 28, 2019, the entire contents of which are incorporated herein by this reference.

BACKGROUND OF THE INVENTION

1. Field of the Invention

The present invention relates to an endoscope configured to perform bending operation by inclining an operation lever, a bending operation mechanism for endoscope configured to perform the bending operation by inclining the operation lever, and an operation portion for endoscope configured to perform the bending operation by inclining the operation lever.

2. Description of the Related Art

There is known an endoscope in a form allowing bending of a bending portion which is provided in an elongated insertion portion insertable into an inside of a human body, a machine, or the like. For example, International Publication No. 2017/145431 discloses an endoscope including an operation portion provided with a joystick lever and a bending portion connected to a plurality of wires. The endoscope can change traction amounts of a plurality of wires in accordance with an inclination direction and an inclination angle of the joystick lever so as to change a bending direction and a bending angle of the bending portion.

The endoscope disclosed in International Publication No. 2017/145431 has a configuration in which the joystick lever is retained by using a pair of screws for a frame-shaped member to penetrate the frame-shaped member so as to retain another member turnably around one axis.

SUMMARY OF THE INVENTION

An endoscope according to an aspect of the present invention includes: a first bearing including a first recess along a first central axis; a second bearing disposed in the first recess and provided with a second central axis intersecting the first central axis, the second bearing including a second recess along the second central axis and being retained turnably around the first central axis; and an operation lever disposed in the second recess, and including a shaft member retained turnably around the second central axis.

A bending operation mechanism for endoscope according to an aspect of the present invention includes: a first bearing including a first recess along a first central axis; a second bearing disposed in the first recess and provided with a second central axis intersecting the first central axis, the second bearing including a second recess along the second central axis and being retained turnably around the first central axis; and an operation lever disposed in the second recess, and including a shaft member retained turnably around the second central axis.

An operation portion for endoscope according to an aspect of the present invention includes: a first bearing including a first recess along a first central axis; a second bearing disposed in the first recess and provided with a second central axis intersecting the first central axis, the second bearing including a second recess along the second central axis and being retained turnably around the first central axis; and an operation lever disposed in the second recess, and including a shaft member retained turnably around the second central axis.

DETAILED DESCRIPTION OF THE PREFERRED EMBODIMENTS

Figure 1:
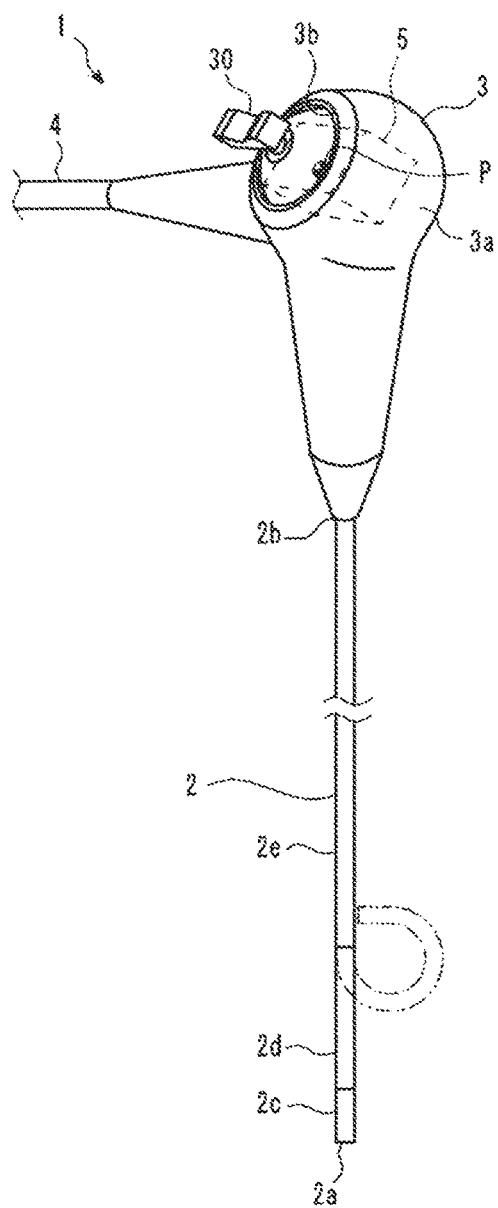
FIG. 1 is a view schematically showing a configuration of an endoscope of a first embodiment.

Hereinafter, preferred embodiments of the present invention will be described with reference to the drawings. Note that in the respective drawings used for following description, different scales may be used for each component member in order to present each component member in a size recognizable in the drawings. The present invention is not limited only to the number of the component members, the shapes of the component members, size ratios of the component members, and relative positional relationships among each of the component members described in the drawings.

First Embodiment

FIG. 1 is a view schematically showing a configuration of an endoscope 1 of a first embodiment. The endoscope 1 includes an insertion portion 2 having an elongated shape that is inserted into a subject, an operation portion 3 interconnected to a proximal end 2b of the insertion portion 2, a connection cable 4 extending from the operation portion 3, and a bending operation mechanism 5 provided in the operation portion 3. The subject into which the insertion portion 2 is inserted may be a living organism such as human being, or may be a non-living organism, such as a machine or a building.

The insertion portion 2 is configured of a distal end portion 2c, a bending portion 2d, and a tubular portion 2e which are interconnected in order from a distal end 2a to the proximal end 2b.

The distal end portion 2c is equipped with an image pickup apparatus, which is not shown. The image pickup apparatus includes an image sensor (imager) and an objective lens, or the like. The distal end portion 2c is provided with an illumination window, not shown, which emits light for illuminating an object of the image pickup apparatus. The connection cable 4 includes a connector that is connected to a processor, which is an external device. An image picked up by the image pickup apparatus is displayed on an image display device connected to the processor. Since the image pickup apparatus and the illumination window are publicly known components, detailed description of the components is omitted.

The bending portion 2d is bent in response to a motion of the operation lever 30 of the bending operation mechanism 5 provided in the operation portion 3. As an example in the present embodiment, the bending operation mechanism 5 has a configuration of transmitting the motion of the operation lever 30 to the bending portion 2d mechanically. The bending portion 2d is connected to distal ends of a plurality of wires 50 (not shown in FIG. 1), and the bending operation mechanism 5 is connected to proximal ends 50a of the plurality of wires 50.

As described later in detail, the bending operation mechanism 5 changes individual traction amounts of the plurality of wires 50 in response to the motion of the operation lever 30. The bending portion 2d changes in direction and angle of bending as the traction amounts of the plurality of wires 50 change. As an example in the present embodiment, the bending operation mechanism 5 changes the traction amounts of four wires 50. The bending portion 2d bends in any directions. The configuration of the bending portion 2d, which changes the direction and the angle of bending in accordance with change in the traction amounts of the plurality of wires 50, is a publicly known configuration, and therefore, detailed description of the configuration is omitted.

Note that the endoscope 1 may be in the form including the bending operation mechanism 5 including an encoder that converts the motion of the operation lever 30 into an electrical signal, and an actuator that generates force to bend the bending portion 2d in response to the electrical signal. In other words, the endoscope 1 is not limited to a form directly transmitting the force applied to the operation lever 30 by a user to the bending portion 2d.

The tubular portion 2e is a tubular area that links the proximal end of the bending portion 2d and the operation portion 3. The tubular portion 2e may have flexibility or may have no flexibility. As an example in the present embodiment, the tubular portion 2e has flexibility, and is flexible enough to be bent according to external force. Endoscopes in a form having a flexible tubular portion are typically referred to as flexible endoscopes, while endoscopes in a form having a rigid tubular portion are typically referred to as rigid endoscopes. Flexible endoscopes and rigid endoscopes in a medical field, for example, are defined in ISO8600-1: 2015.

The operation portion 3 includes a cover member 3a, which is a hollow body portion that houses the bending operation mechanism 5 inside. The cover member 3a has an opening 3b formed to extend from the outside to the inside. A distal end portion 30a of the operation lever 30 is an extension member extending to the outside of the operation portion 3 from the opening 3b.

The cover member 3a is the part that is gripped by the user. As described later, the operation lever 30 is swingably supported to the cover member 3a. The operation lever 30 is provided at a position where the user can apply force to the distal end portion 30a with a finger of the user.

As an example in the present embodiment shown in FIG. 1, the operation lever 30 is inserted into the opening 3b, and the distal end portion 30a of the operation lever 30 protrudes outward from the outer surface of the cover member 3a. At an end portion of the distal end portion 30a that is the extension member, a finger contact member 30b, which is the part where the user touches the operation lever 30, is provided.

Note that the shape and the arrangement of the operation lever 30 are not limited to the shape and the arrangement in the present embodiment. For example, the distal end portion 30a of the operation lever 30 may be positioned inside the outer surface of the cover member 3a. In this case, the user may insert a finger into the opening 3b and touches the distal end portion 30a of the operation lever 30.

The operation lever 30 swings around a prescribed support point P which is fixed to the cover member 3a. A bending direction and a bending angle of the bending portion 2d change in accordance with an inclination direction (inclination orientation) and an inclination angle of the operation lever 30 from a neutral position. The neutral position of the operation lever 30 is a prescribed position within a turnable range of the operation lever 30. In the present embodiment, the neutral position of the operation lever 30 is the position where the shape of the bending portion 2d is linear. In the state where the operation lever 30 is in the neutral position, the distal end portion 30a of the operation lever 30 is approximately at the center of the opening 3b as viewed in an opening direction of the opening 3b.

Figure 2:
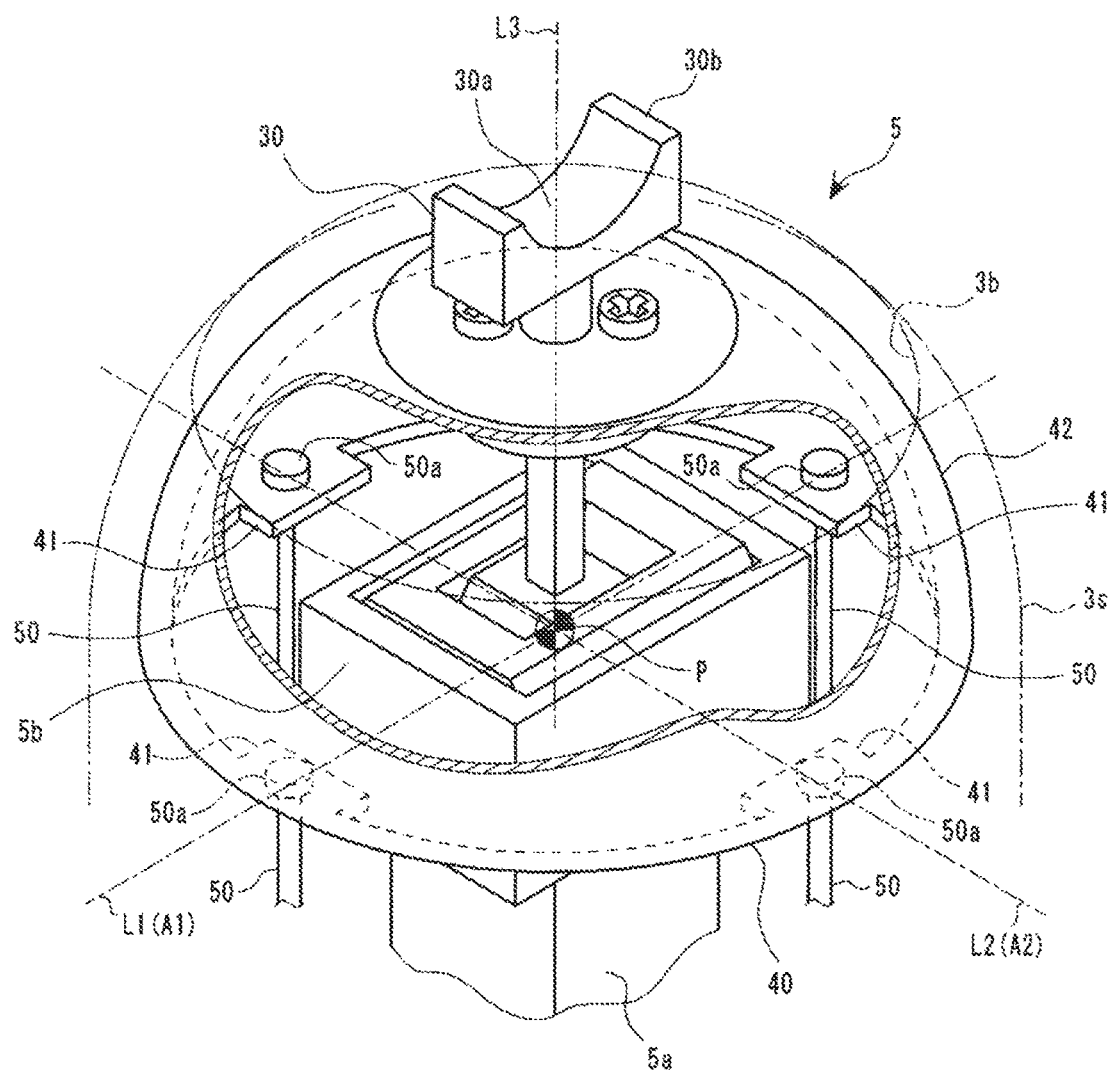
FIG. 2 is a perspective view of a bending operation mechanism of the first embodiment.
Figure 3:
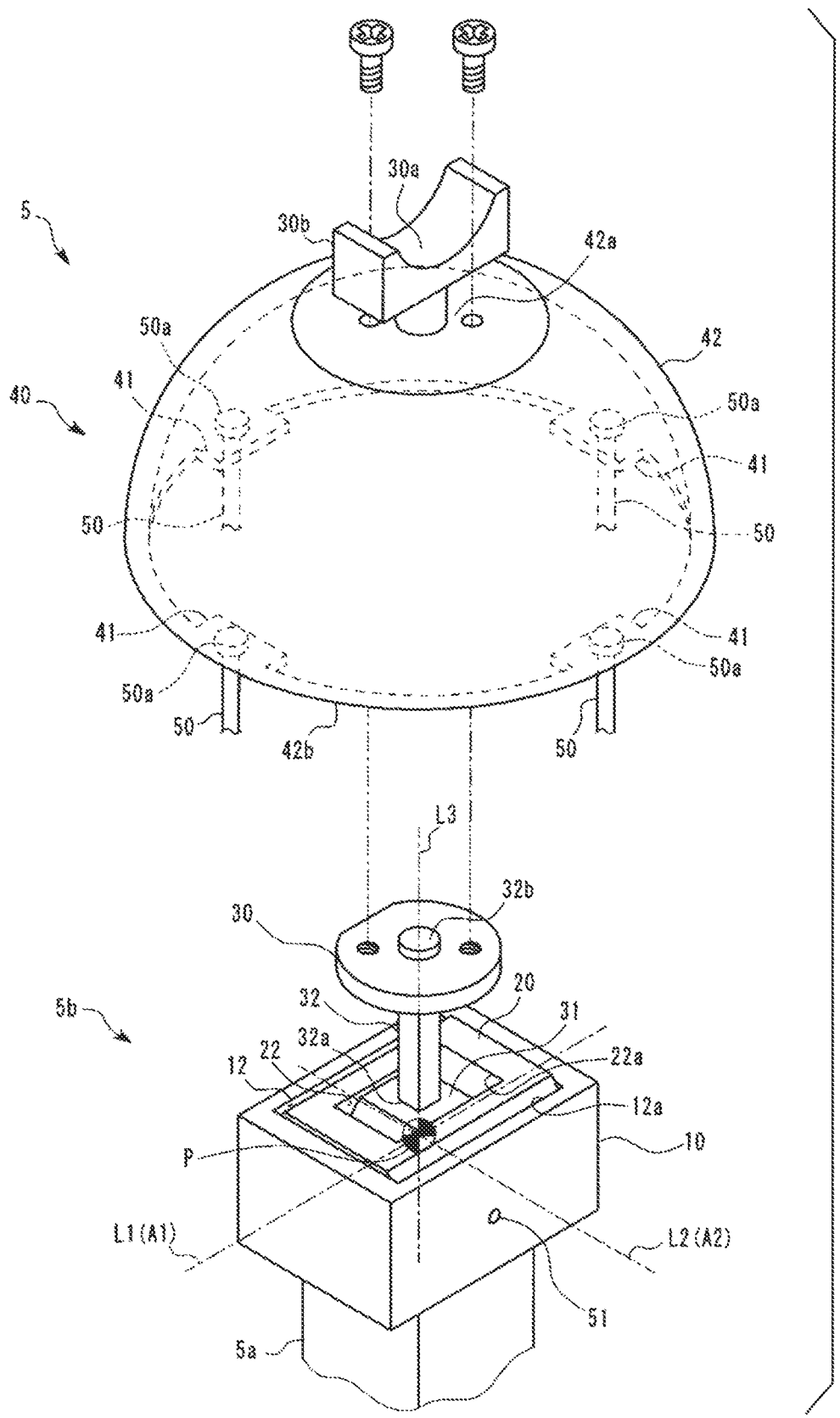
FIG. 3 is an exploded perspective view of the bending operation mechanism of the first embodiment.
Figure 4:
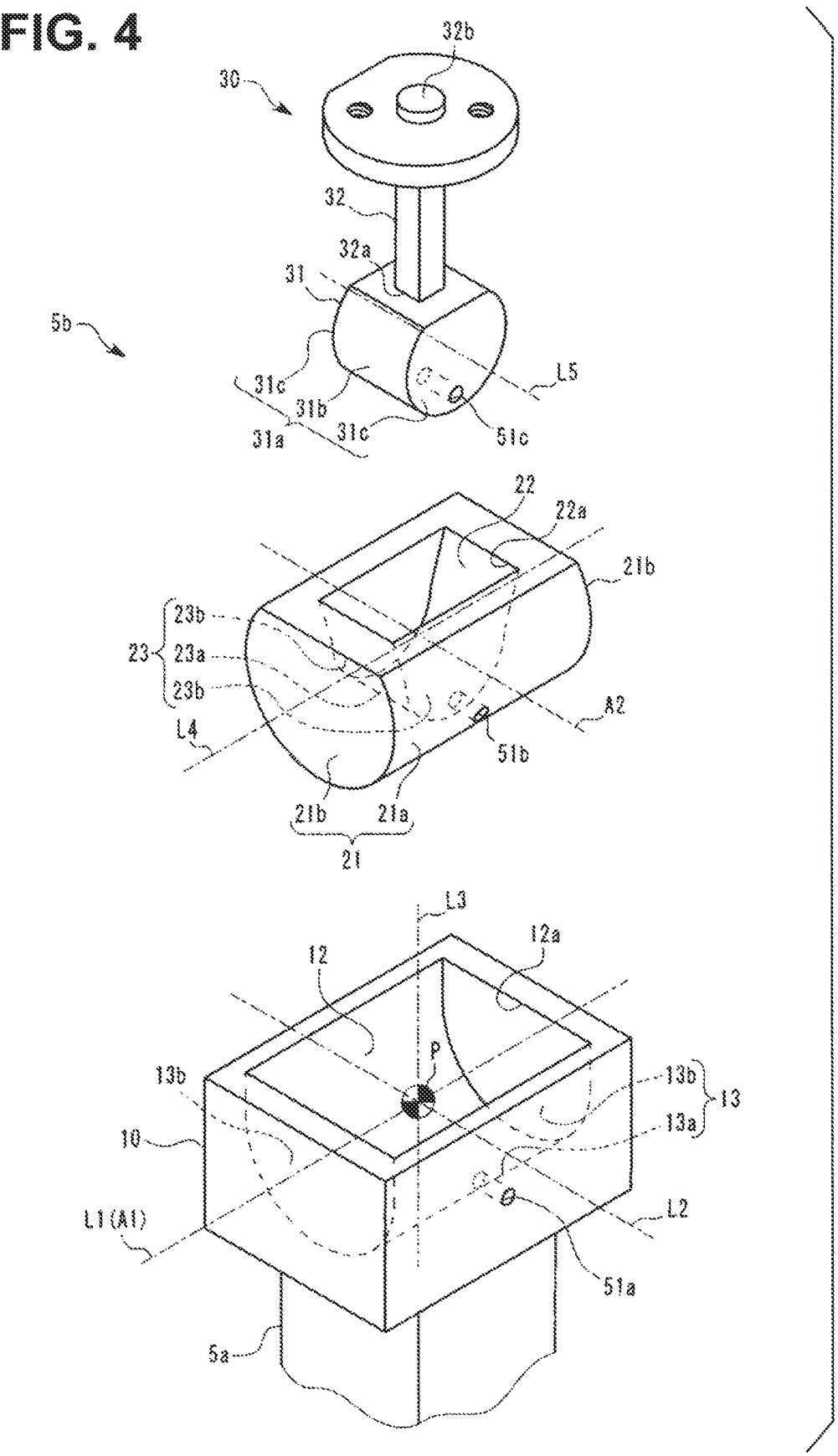
FIG. 4 is an exploded perspective view of a bearing portion of the first embodiment.

FIG. 2 is a perspective view of the bending operation mechanism 5. FIG. 3 is an exploded perspective view of the bending operation mechanism 5. FIG. 4 is an exploded perspective view of a bearing portion 5b. The bending operation mechanism 5 includes a base portion 5a, the bearing portion 5b, the operation lever 30, and a wire traction portion 40. Hereinafter, with respect to the operation lever 30, an axis extending from the support point P to the distal end portion 30a is referred to as a longitudinal axis of the operation lever 30.

The base portion 5a is fixed to the cover member 3a of the operation portion 3. The bearing portion 5b includes a bearing. The bearing includes a bottomed recess having an opening in a prescribed direction. Inside the recess of the bearing, a turning member is disposed turnably with respect to the recess. The turning member is inserted into the recess through the opening. The operation lever 30 includes a lever member 32 having a proximal end 32a, which is a first end, interconnected to the turning member. The lever member 32 is provided so as to extend from the proximal end 32a to the outside of the recess opening along the longitudinal axis of the operation lever 30. The distal end 32b of the lever member 32 is positioned outside the recess opening.

The bearing portion 5b has a mechanism that retains the operation lever 30 turnably around the support point P, while restricting the operation lever 30 from turning around the longitudinal axis with respect to the base portion 5a. More specifically, the bearing portion 5b retains the operation lever 30 turnably around two linear axes including a first central axis A1 and a second central axis A2, relative to the base portion 5a. The first central axis A1 and the second central axis A2 intersect at a prescribed angle at the support point P. As an example in the present embodiment, the first central axis A1 and the second central axis A2 are orthogonal at the support point P. The second central axis A2 turns around the first central axis A1 with respect to the base portion 5a.

In following description, three linear axes are defined. The positions of the three linear axes relative to the base portion 5a are fixed, and the three axes are orthogonal to each other at the support point P. A first linear axis L1 is an axis coincident with the first central axis A1. A second linear axis L2 is coincident with the second central axis A2 in the state where the operation lever 30 is in the neutral position. A third linear axis L3 is coincident with the longitudinal axis of the operation lever 30 in the state where the operation lever 30 is in the neutral position.

The third linear axis L3 passes inside the opening 3b. A direction extending from the support point P to the opening 3b along the third linear axis L3 is referred to as an outward direction (first direction), and a direction opposite to the outward direction is referred to as an inward direction.

Figure 5:
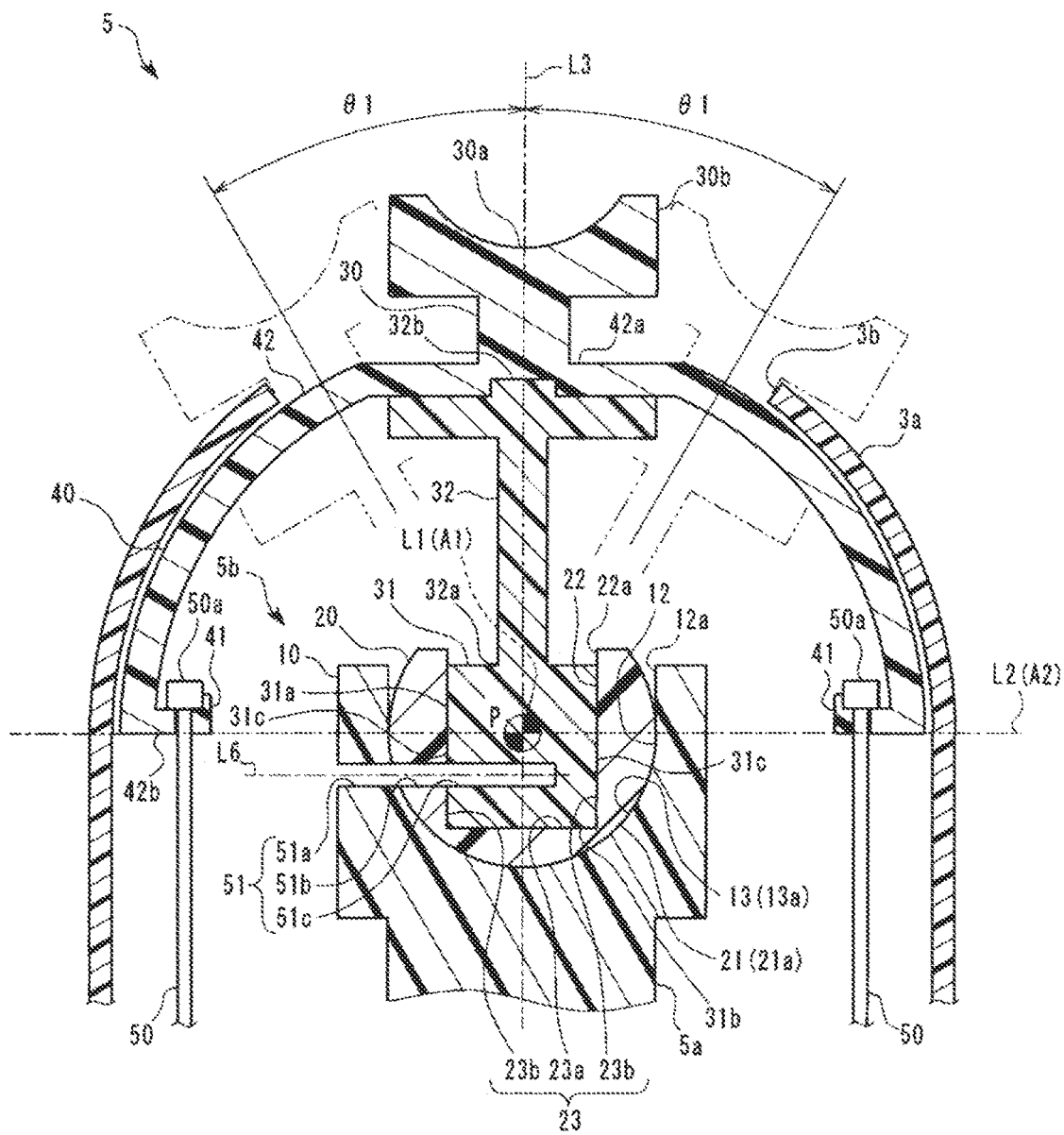
FIG. 5 is a sectional view of the bending operation mechanism of the first embodiment in a plane including a second linear axis and a third linear axis.
Figure 6:
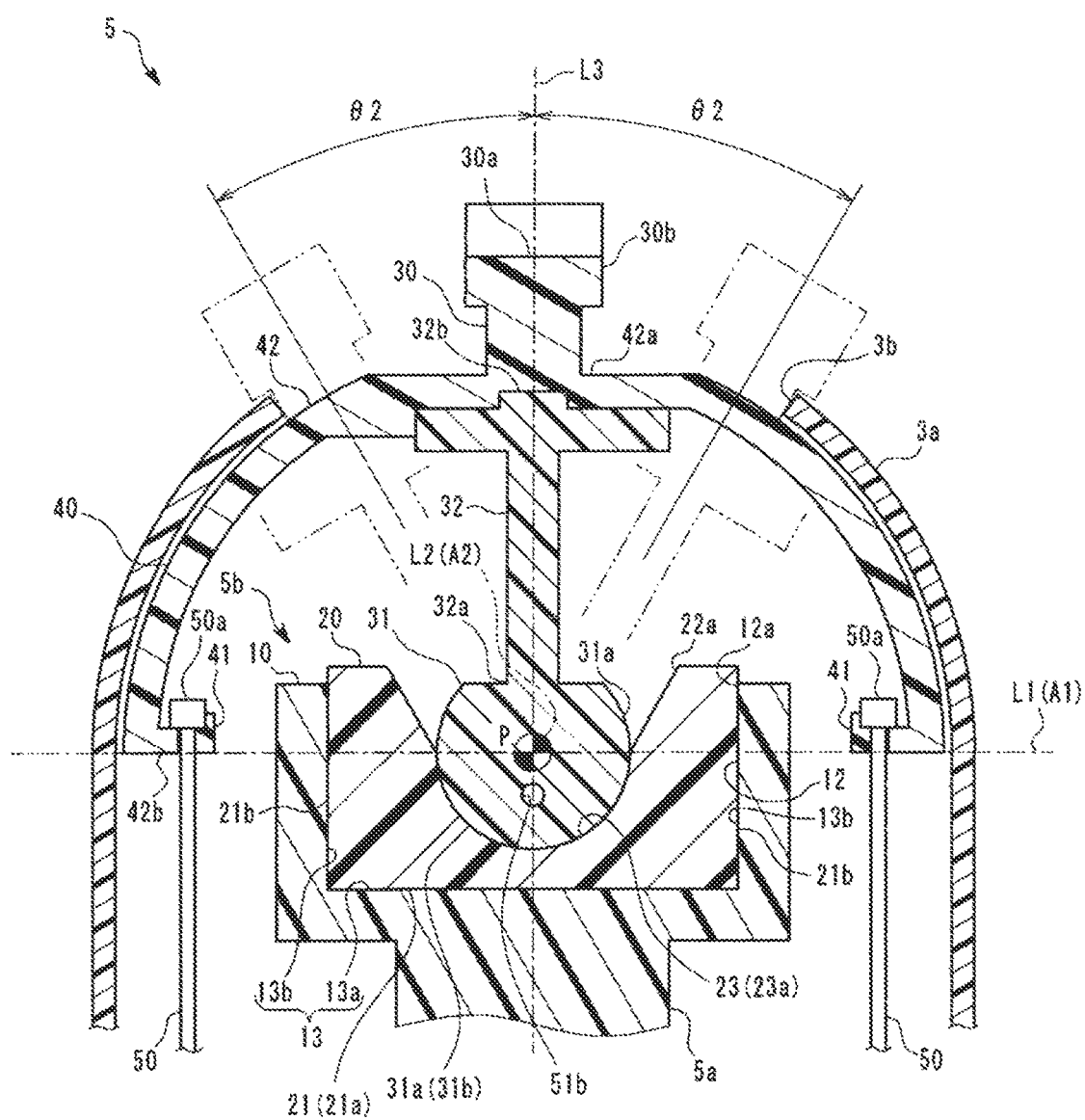
FIG. 6 is a sectional view of the bending operation mechanism of the first embodiment in a plane including a first linear axis and the third linear axis.

FIG. 5 is a sectional view of the bending operation mechanism 5 in a plane (L2-L3 plane) including the second linear axis L2 and the third linear axis L3. FIG. 6 is a sectional view of the bending operation mechanism 5 in a plane (L1-L3 plane) including the first linear axis L1 and the third linear axis L3. FIGS. 5 and 6 show the state where the operation lever 30 is in the neutral position.

In the present embodiment, for the sake of description, the inclination angle of the operation lever 30 is defined as the angle at which the longitudinal axis of the operation lever 30 and the third linear axis L3 intersect at the support point P.

The operation lever 30 includes the lever member 32 and a shaft member 31 which is a turning member. The shaft member 31 is an area retained by the bearing portion 5b. The lever member 32 is a column-shaped member provided to extend along the longitudinal axis. The proximal end 32a of the lever member 32 is fixed to the shaft member 31. The shaft member 31 and the lever member 32 are integrally molded. The lever member 32 extends from the outer surface of the shaft member 31 in a direction orthogonal to the second central axis A2.

Materials of the shaft member 31 and the lever member 32, which are molded integrally, are not particularly limited. As an example in the present embodiment, the shaft member 31 and the lever member 32 are made of resin such as engineering plastic. Note that the shaft member 31 and the lever member 32 are made of metal and may be molded by casting or forging, or may be molded by sintering powder metal.

The distal end 32b of the lever member 32 is fixed to the finger contact member 30b, which configures the distal end portion 30a of the operation lever 30.

The wire traction portion 40 is fixed to the operation lever 30. Therefore, the wire traction portion 40, along with the operation lever 30, turns around the first central axis A1 and the second central axis A2, relative to the base portion 5a.

The wire traction portion 40 includes a plurality of retention members 41 which retain respective proximal ends 50a of the plurality of wires 50.

In the present embodiment, the wire traction portion 40 includes four retention members 41 which retain the proximal ends 50a of the four wires 50. As described above, the distal ends of the four wires 50 are fixed to the bending portion 2d. The four retention members 41 are arranged on a circle having a prescribed radius and centered on the longitudinal axis on a plane orthogonal to the longitudinal axis of the operation lever 30. As an example in the present embodiment, the four retention members 41 are evenly arranged on a circle centered on the longitudinal axis, though the four retention members 41 on the circle may be unevenly distanced.

The plurality of wires 50 are inserted into the insertion portion 2 and the cover member 3a of the operation portion 3. The vicinity of each proximal end 50a of the plurality of wires 50 is routed such that each longitudinal direction extends along the third linear axis L3 in the cover member 3a. In other words, the plurality of wires 50 extend in the inward direction from the proximal ends 50a fixed to the plurality of retention members 41 along the third linear axis L3.

In accordance with turning of the operation lever 30 around the support point P, the plurality of retention members 41 turn around the support point P relative to the base portion 5a, while maintaining the respective relative positions. This movement of the plurality of retention members 41 changes the traction amounts of the plurality of wires 50.

In the wire traction portion 40, the configuration of fixing the plurality of retention members 41 to the operation lever 30 is not particularly limited. As an example in the present embodiment, the wire traction portion 40 includes a substantially half-hemispherical dome member 42 centered on the support point P. The dome member 42 is hollow. The distal end 32b of the lever member 32 is fixed to an inner circumferential surface side of a top portion 42a of the dome member 42. The plurality of retention member 41 are provided on a bottom portion 42b of the dome member 42.

The finger contact member 30b is fixed to an outer circumferential surface of the top portion 42a of the dome member 42. In other words, the dome member 42 is part of the operation lever 30. As shown in FIGS. 5 and 6, part of the outer circumferential surface of the dome member 42 is exposed to the outside of the operation portion 3 via the opening 3b provided in the cover member 3a.

An outer diameter of the dome member 42 is smaller than a maximum width of the opening 3b. Therefore, the dome member 42 cannot pass through the opening 3b. The dome member 42 is fixed to the operation lever 30 as described above. Therefore, the cover member 3a, which is part of an exterior, abuts and interferes with a distal end side of the operation lever 30 (dome member 42) so as to restrict movement of the operation lever 30 in a direction away from the support point P along the longitudinal axis. The direction away from the support point P along the longitudinal axis of the operation lever 30 is a longitudinal axis direction extending from the proximal end 32a of the lever member 32 to the distal end 32b. The distal end side of the operation lever 30 may abut a member other than the cover member 3a. For example, the distal end side of the operation lever 30 may be configured to abut an interior member which is provided inside the cover member 3a and constitutes part of the body portion. The cover member 3a is a stopper configured to restrict movement of the operation lever 30 in the longitudinal axis direction.

When an edge of the opening 3b interferes with the finger contact member 30b, the turning range of the operation lever 30 around the support point P in the dome member 42 is limited. In other words, the cover member 3a interferes with the operation lever 30 (finger contact member 30b), and thereby restricts the turnable range of the operation lever 30 around the support point P.

As shown in FIG. 5, an absolute value of a maximum inclination angle when the operation lever 30 turns around the first central axis A1 is defined as a first limit angle θ1. As shown in FIG. 6, an absolute value of a maximum inclination angle when the operation lever 30 turns around the second central axis A2 is defined as a second limit angle θ2. Depending on an opening shape of the opening 3b, the maximum inclination angle of the operation lever 30 is larger than the first limit angle θ1 and the second limit angle θ2. As an example in the present embodiment, the first limit angle θ1 and the second limit angle θ2 are values equal to or less than 45 degrees.

In the present embodiment, a spherical outer circumferential surface of the dome member 42 is always provided in a range of closing the opening 3b when the operation lever 30 is within the range turnable around the support point P. Therefore, the dome member 42 is a member that fixes the plurality of retention members 41 to the operation lever 30 and is also a member that prevents foreign objects or user's fingers from entering into the inside of the cover member 3a through the opening 3b. Note that the dome member 42 may be divided into a plurality of members.

The configuration of fixing the plurality of retention members 41 to the operation lever 30 is not limited to the configuration of the present embodiment. For example, the wire traction portion 40 may be configured to include a plurality of arm portions extending from the operation lever 30 in a direction orthogonal to the longitudinal axis, and the plurality of retention members 41 may be provided at each distal end of the arm portions.

The configuration of the bearing portion 5b and the shaft member 31 will be described. The bearing portion 5b includes a first bearing 10 and a second bearing 20.

Schematically, the first bearing 10, which is fixed to the base portion 5a, is a slide bearing that supports part of an outer outline of the second bearing 20 as a shaft. The second bearing 20 is a slide bearing that supports part of an outer outline of the shaft member 31 as a shaft. As described before, the shaft member 31 is molded integrally with the lever member 32 of the operation lever 30.

The first bearing 10 retains the second bearing 20 turnably around the first central axis A1 with respect to the base portion 5a, and restricts the second bearing 20 from moving relative to the base portion 5a in a direction parallel to the first central axis A1. In other words, the first bearing 10 receives load applied to the second bearing 20 in a radial direction and a thrust direction.

The first bearing 10 is molded integrally with the base portion 5a. A material of the first bearing 10 and the base portion 5a, which are molded integrally, is not particularly limited. As an example in the present embodiment, the first bearing 10 and the base portion 5a are made of resin such as engineering plastic. Note that the first bearing 10 and the base portion 5a are made of metal and may be molded by casting or forging, or may be molded by sintering powder metal.

The second bearing 20 retains the shaft member 31 turnably around the second central axis A2 with respect to the second bearing 20, and restricts the shaft member 31 from moving relative to the second bearing 20 in a direction parallel to the second central axis A2. In other words, the second bearing 20 receives load applied to the shaft member 31 in the radial direction and the thrust direction.

The position of the second central axis A2 relative to the second bearing 20 is fixed. The second central axis A2, together with the second bearing 20, turns around the first central axis with respect to the base portion 5a.

The second bearing 20 is a molded part. The material of the second bearing 20 is not particularly limited. As an example in the present embodiment, the second bearing 20 is made of resin such as engineering plastic. Note that the second bearing 20 is made of metal and may be molded by casting or forging, or may be molded by sintering powder metal.

As shown in FIG. 4, a first recess 12 is formed in the first bearing 10. The first bearing 10 includes the first recess 12 along the first central axis A1. The first recess 12 is a bottomed hole that is open in the outward direction, which is the first direction along the third linear axis L3, in the state where the first bearing 10 is fixed to the base portion 5a. In other words, a depth direction of the first recess 12 is the inward direction.

The shape of the opening 12a of the first recess 12 is large enough to allow insertion of the second bearing 20 into the first recess 12. Specifically, the size of the opening 12a of the first recess 12 is larger than a projected shape of the second bearing 20 onto the L1-L2 plane when the operation lever 30 is at the neutral position.

Inside the first recess 12, a sliding portion 13 that slides against part of an outer surface of the second bearing 20 is formed. The sliding portion 13 includes a radial bearing portion 13a and thrust bearing portions 13b.

The radial bearing portion 13a receives load applied to the second bearing 20 in the radial direction, and retains the second bearing 20 turnably around the first central axis A1, in the state where the second bearing 20 is disposed in the first recess 12.

The radial bearing portion 13a is formed on a bottom portion of the first recess 12 with the inward direction as a depth direction, and the first recess 12 has an opening shape larger than the second bearing 20. Accordingly, the radial bearing portion 13a can receive the load applied to the second bearing 20 in the inward direction, but cannot receive the load applied to the second bearing 20 in the outward direction.

The radial bearing portion 13a in the present embodiment can receive the load in the radial direction in the range where the absolute value of inclination with respect to the third linear axis L3 is equal to or less than the first limit angle θ1 at least on the L2-L3 plane with the inward direction as the center.

In other words, when the inclination angle of the operation lever 30 around the first central axis A1 is within the first limit angle θ1, the first bearing 10 can receive force of pushing the operation lever 30 toward the support point P.

More specifically, the radial bearing portion 13a in the present embodiment is a cylindrical surface with a prescribed internal diameter Di1 centered on the first central axis A1. The cylindrical surface is a semi-circular shape that is formed downward from the L1-L2 plane. In other words, the first recess 12 of the first bearing 10 has a semi-cylindrical bottom surface formed along the first central axis A1.

The thrust bearing portions 13b in the present embodiment are a pair of planar wall surfaces facing each other across the radial bearing portion 13a and orthogonal to the first central axis A1. The thrust bearing portions 13b receive the load applied to the second bearing 20 in the thrust direction, and restrict the movement of the second bearing 20 in the direction parallel to the first central axis A1, in the state where the second bearing 20 is disposed in the first recess 12.

Note that the surface of the radial bearing portion 13a and the thrust bearing portions 13b may be provided with grooves and holes for the purpose of preventing biting of foreign materials, retaining lubricants, or the like.

As shown in FIG. 4, the outline of the second bearing 20 supported by the first bearing 10 partially includes a cylindrical shape portion 21 having a prescribed fourth linear axis L4 as a central axis. The fourth linear axis L4 is orthogonal to the second central axis A2. In the state where the second bearing 20 is disposed in the first recess 12, the fourth linear axis L4 approximately coincides with the first central axis A1.

At least part of the outer surface of the cylindrical shape portion 21 serves as a sliding surface against the first bearing 10. The outer surface of the cylindrical shape portion 21 includes a cylindrical surface 21a and a pair of end faces 21b.

The cylindrical surface 21a has a prescribed first outer diameter Do1. The first outer diameter Do1 is smaller than the inner diameter Di1 of the radial bearing portion 13a. The first outer diameter Do1 is set to a value that allows the cylindrical surface 21a to fit into the radial bearing portion 13a with a prescribed gap and to slide against the radial bearing portion 13a.

The end faces 21b are flat surfaces orthogonal to the fourth linear axis L4. The end faces 21b face outside in directions opposite to each other across the cylindrical surface 21a. The end faces 21b are slidably in contact with the thrust bearing portion 13b, in the state where the second bearing 20 is disposed in the first recess 12.

A second recess 22 is formed in the second bearing 20. The second recess 22 is a bottomed hole that is open in a direction orthogonal to the second central axis A2 and the fourth linear axis L4. The second recess 22 is open in the outward direction along the third linear axis L3, in the state where the second bearing 20 is disposed in the first recess 12 and the operation lever 30 is in the neutral position.

The shape of the opening 22a of the second recess 22 is large enough to allow insertion of the shaft member 31 into the second recess 22. Specifically, the size of the opening 22a of the second recess 22 is larger than a projected shape of the shaft member 31 onto the L1-L2 plane when the operation lever 30 is in the neutral position.

Inside the second recess 22, a sliding portion 23 that slides against part of an outer surface of the shaft member 31 is formed. The sliding portion 23 includes a radial bearing portion 23a and a thrust bearing portion 23b.

The radial bearing portion 23a receives the load applied to the shaft member 31 in the radial direction, and retains the shaft member 31 turnably around the second central axis A2, in the state where the shaft member 31 is disposed in the second recess 22.

As described in the foregoing, the second bearing 20 is disposed in the first recess 12 and provided with the second central axis A2 intersecting the first central axis A1, the second bearing 20 including the second recess 22 along the second central axis A2 and being retained turnably around the first central axis A1. The operation lever 30 is disposed in the second recess 22, and includes the shaft member 31 retained turnably around the second central axis A2.

The radial bearing portion 23a is formed on a bottom portion of the second recess 22, and the second recess 22 has an opening shape larger than the shaft member 31. Accordingly, the radial bearing portion 23a can receive the load applied to the shaft member 31 in a depth direction of the second recess 22, but cannot receive the load applied to the shaft member 31 in an opening direction of the second recess 22. Here, the depth direction of the second recess 22 is the direction extending from the opening to the bottom portion of the second recess 22 along an axis orthogonal to the second central axis A2 and the fourth linear axis L4. The depth direction of the second recess 22 coincides with the downward direction, in the state where the operation lever 30 is in the neutral position.

The radial bearing portion 23a in the present embodiment can receive at least the load in the radial direction in the range where the absolute value of inclination with respect to the depth direction of the second recess 22 is equal to or less than the second limit angle θ2 on the plane orthogonal to the second central axis A2.

In other words, when the inclination angle of the operation lever 30 around the second central axis A2 is within the second limit angle θ2 in the state where the second bearing 20 is disposed in the first recess 12 and the shaft member 31 is disposed in the second recess 22, the second bearing 20 can receive force of pushing the operation lever 30 toward the support point P.

More specifically, the radial bearing portion 23a in the present embodiment is a cylindrical surface with a prescribed internal diameter Di2 centered on the second central axis A2. The cylindrical surface has a semi-circular shape that is formed in the depth direction from the A2-L4 plane. In other words, the second recess 22 of the second bearing 20 has a semi-cylindrical bottom surface formed along the second central axis A2.

The thrust bearing portions 23b in the present embodiment are a pair of planar wall surfaces facing each other across the radial bearing portion 23a and orthogonal to the second central axis A2. The thrust bearing portion 23b receives the load applied to the shaft member 31 in the thrust direction, and restricts the movement of the shaft member 31 in the direction parallel to the second central axis A2, in the state where the shaft member 31 is disposed in the second recess 22.

Note that the surfaces of the radial bearing portion 23a and the thrust bearing portion 23b may be provided with grooves and holes for the purpose of preventing biting of foreign materials, retaining lubricants, or the like.

The outline of the shaft member 31 supported by the second bearing 20 partially includes a cylindrical shape portion 31a having a prescribed fifth linear axis L5 as a central axis. The fifth linear axis L5 is orthogonal to the longitudinal axis of the lever member 32. In the state where the shaft member 31 is disposed in the second recess 22, the fifth linear axis L5 approximately coincides with the second central axis A2.

At least part of the outer surface of the cylindrical shape portion 31a serves as a sliding surface against the second bearing 20. The outer surface of the cylindrical shape portion 31a includes a cylindrical surface 31b and a pair of end faces 31c.

The cylindrical surface 31b has a prescribed second outer diameter Do2. The second outer diameter Do2 is smaller than the inner diameter Di2 of the radial bearing portion 23a. The second outer diameter Do2 is set to a value that allows the cylindrical surface 31b to fit into the radial bearing portion 23a with a prescribed gap and to slide against the radial bearing portion 23a.

The end faces 31c are flat faces orthogonal to the fifth linear axis L5. The end faces 31c face outside in the directions opposite to each other across the cylindrical surface 31b. The end faces 31c are slidably in contact with the thrust bearing portion 23b in the state where the shaft member 31 is disposed in the second recess 22.

As described in the foregoing, the bearing portion 5b is configured of three members including the first bearing 10, the second bearing 20, and the shaft member 31, each of which can be manufactured by molding at low costs. Since assembling of the bearing portion 5b is completed by simply combining the three members so as to be stacked in one direction, the assembling is completed in a fewer procedures. Therefore, the bending operation mechanism 5 for the endoscope 1 in the present embodiment can be manufactured at low costs.

As shown in FIGS. 4, 5 and 6, the bearing portion 5b in the present embodiment includes one or more holes 51.

One hole 51 is configured of a first hole 51a formed in the first bearing 10, a second hole 51b formed in the second bearing 20, and a third hole 51c formed in the shaft member 31.

The first hole 51a, the second hole 51b, and the third hole 51c have a generally similar shape in cross-section. As an example in the present embodiment, the first hole 51a, the second hole 51b, and the third hole 51c have a circular cross-sectional shape with the same inner diameter.

The first hole 51a, the second hole 51b, and the third hole 51c are arranged at positions where respective central axes approximately coincide with a sixth linear axis L6 and are aligned in series along the sixth linear axis L6, in the state where the operation lever 30 is in the prescribed position. In other words, one hole 51 is configured when the operation lever 30 is at the prescribed position, and the first hole 51a, the second hole 51b, and the third hole 51c formed in three members are aligned on the same straight line and communicate with each other. As an example in the present embodiment, the first hole 51a, the second hole 51b, and the third hole 51c are aligned in series along the sixth linear axis L6 in the state where the operation lever 30 is in the neutral position.

The position of the sixth linear axis L6 relative to the first bearing 10 is fixed. The sixth linear axis L6 is disposed so as to satisfy either a condition of not passing through the support point P or a condition of passing through the support point P but not in parallel with both the first central axis A1 and the second linear axis L2.

As an example in the present embodiment, the sixth linear axis L6 is disposed so as to satisfy the condition of not passing through the support point P, as shown in FIGS. 5 and 6. In other words, the sixth linear axis L6 is apart from the first central axis A1 and the second central axis A2 in the state where the operation lever 30 is in the neutral position.

The first hole 51a linearly extends from the outer surface of the first bearing 10 to the inner circumferential face of the first recess 12 with the sixth linear axis L6 as the central axis. Note that the first hole 51a may pass through the entire first bearing 10 through the first recess 12.

The first hole 51a linearly extends from the outer surface of the second bearing 20 to the inner circumferential face of the second recess 22. Note that the second hole 51b may pass through the entire second bearing 20 through the second recess 22.

The third hole 51c is a linear hole that is open to the outer surface of the shaft member 31. The third hole 51c may extend or may not extend through the shaft member 31.

As described in the foregoing, the bearing portion 5b includes one or more holes 51 having a depth to at least the shaft member 31 from the outer surface of the first bearing 10 in the state where the operation lever 30 is in the prescribed position.

Figure 7:
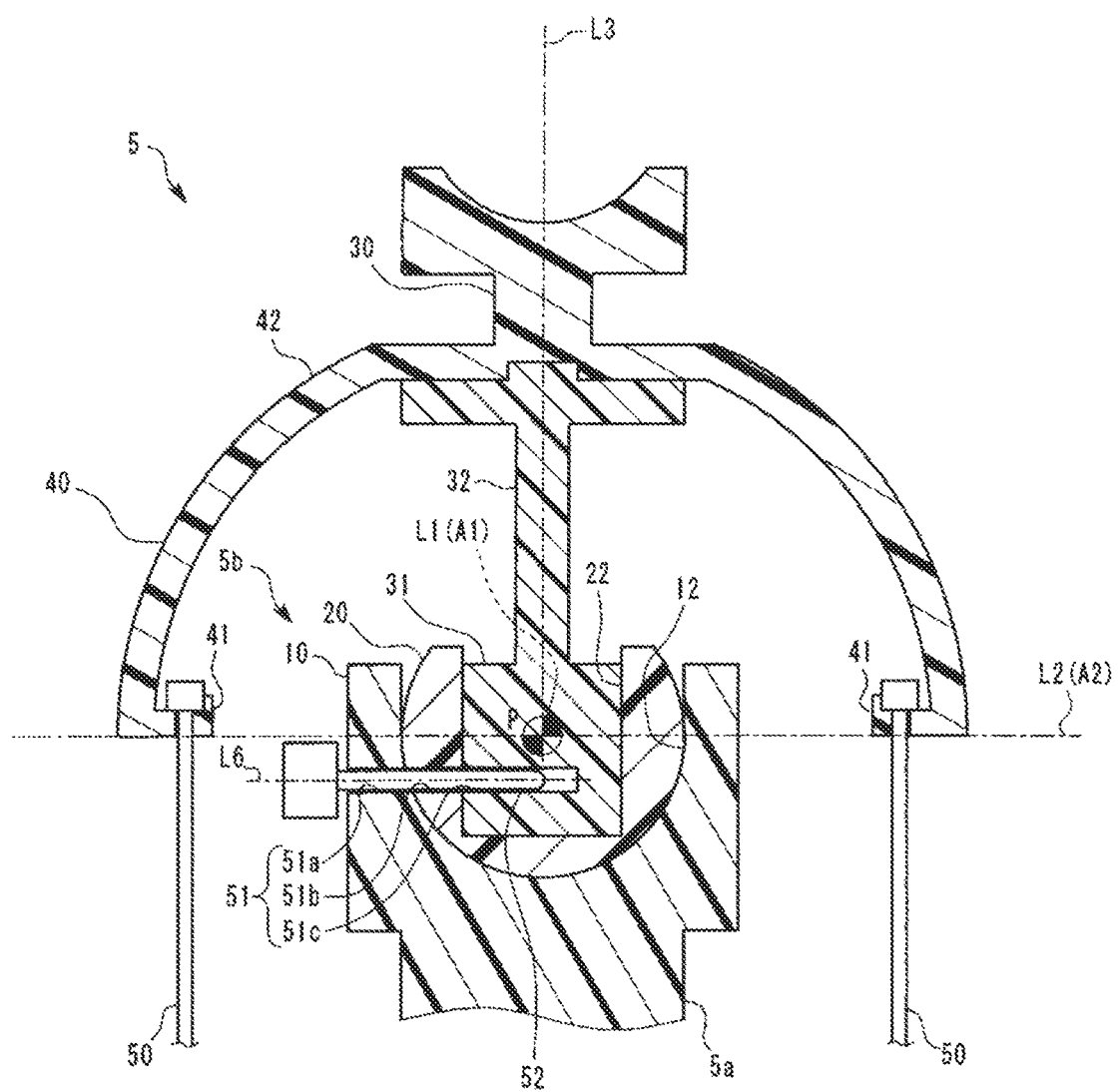
FIG. 7 is a sectional view showing holes inserted with a pin in the bending operation mechanism of the first embodiment.

Inside the hole 51, one pin 52 can be inserted as shown in FIG. 7, provided that the operation lever 30 is in the state of being at the prescribed position. In other words, the bearing portion 5b in the present embodiment is configured of the first bearing 10, the second bearing 20, and the shaft member 31, which include the holes 51a, 51b, and 51c, respectively, to accept the one pin 52 at the same time.

As described before, the hole 51 is disposed so as to satisfy either the condition of not passing through the support point P or the condition of passing through the support point P but not in parallel with both the first central axis A1 and the second linear axis L2. Therefore, the pin 52 inserted in the hole 51 is a stopper that restricts the movement of the second bearing 20 and the shaft member 31 relative to the first bearing 10.

In the present embodiment, the operation lever 30 can be fixed in the neutral position by inserting the pin 52 into the hole 51. For example, when the operation lever 30 can temporarily be fixed in the neutral position during assembling of the endoscope 1, it becomes possible to easily adjust the tension applied to the plurality of wires 50.

By inserting the pin 52 into the hole 51, it is also possible to prevent the second bearing 20 and the shaft member 31 from dropping off from the first bearing 10. The bearing portion 5b has a configuration that does not restrict the second bearing 20 and the shaft member 31 from moving in the outward direction from the first bearing 10. However, when separation of the bearing portion 5b is temporarily prevented at the time of assembling the endoscope 1, it becomes possible to easily perform an assembling work of the bearing portion 5b to the cover member 3a.

As described in the foregoing, since the bearing portion 51b in the present embodiment includes the hole 51, it becomes possible to facilitate the assembling work of the bending operation mechanism 5.

In the above description, the pin 52 is not a member included in the endoscope 1 in a completed state, but is a member temporarily used at the time of assembling the endoscope 1. However, the pin 52 may be a member included in the endoscope 1 at shipment from a factory. For example, the pin 52 may be in the state of being inserted into the hole 51 when the endoscope 1 is shipped from the factory, and may be in such a form that a user of the endoscope 1 removes the pin 52 from the hole 51 at the time of starting to use the endoscope 1. In this case, from shipment from the factory to delivery to the user, operation of the operation lever 30 and the bending portion 2d is in a locked state with the pin 52, which can prevent damage to these mechanisms during transportation of the endoscope 1.

Second Embodiment

Hereinafter, a second embodiment of the present invention will be described. In the following description, only the differences from the first embodiment will be described, and component members similar to the component members of the first embodiment will be designated by the same signs to omit the description as appropriate.

Figure 8:
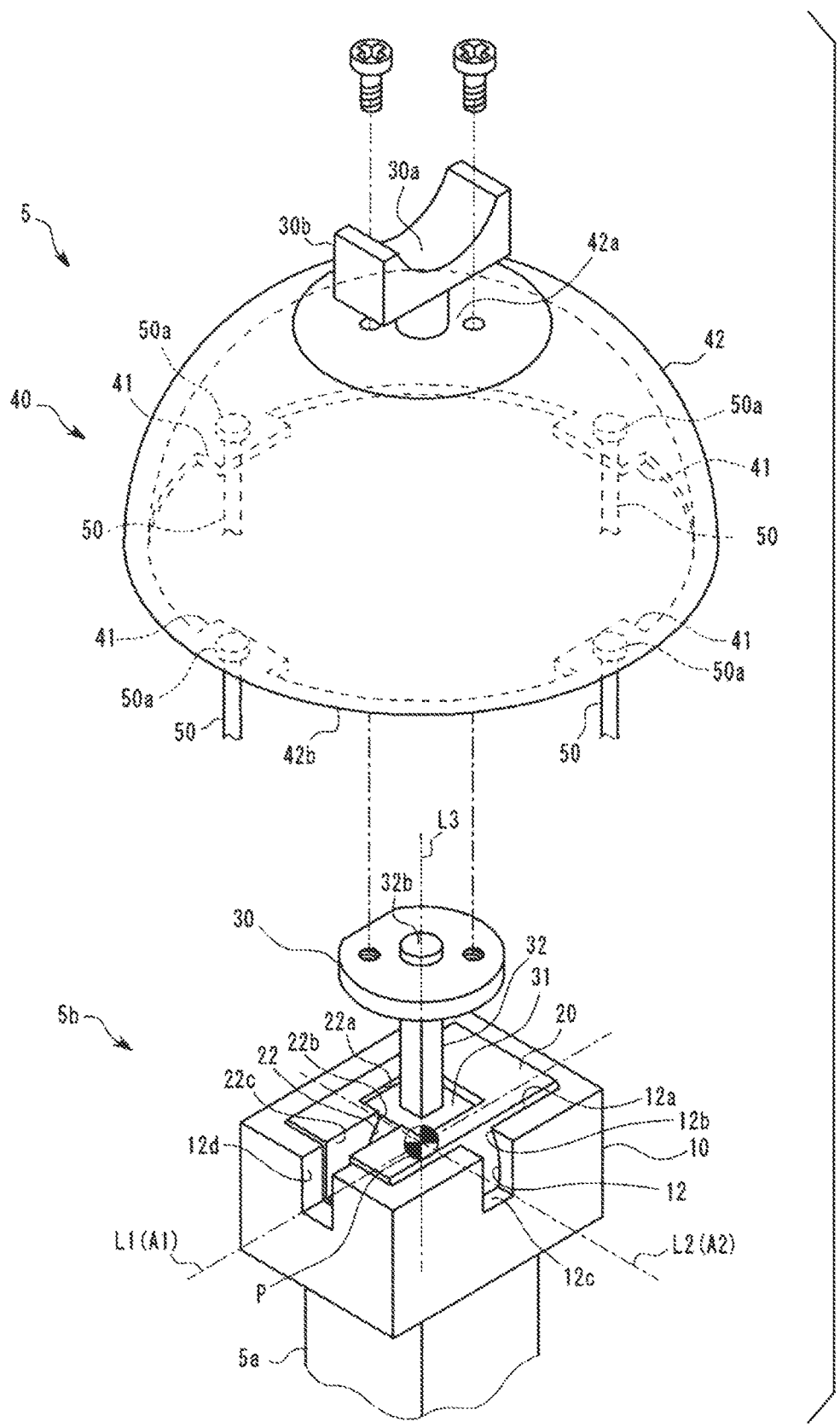
FIG. 8 is an exploded perspective view of a bending operation mechanism of a second embodiment.
Figure 9:
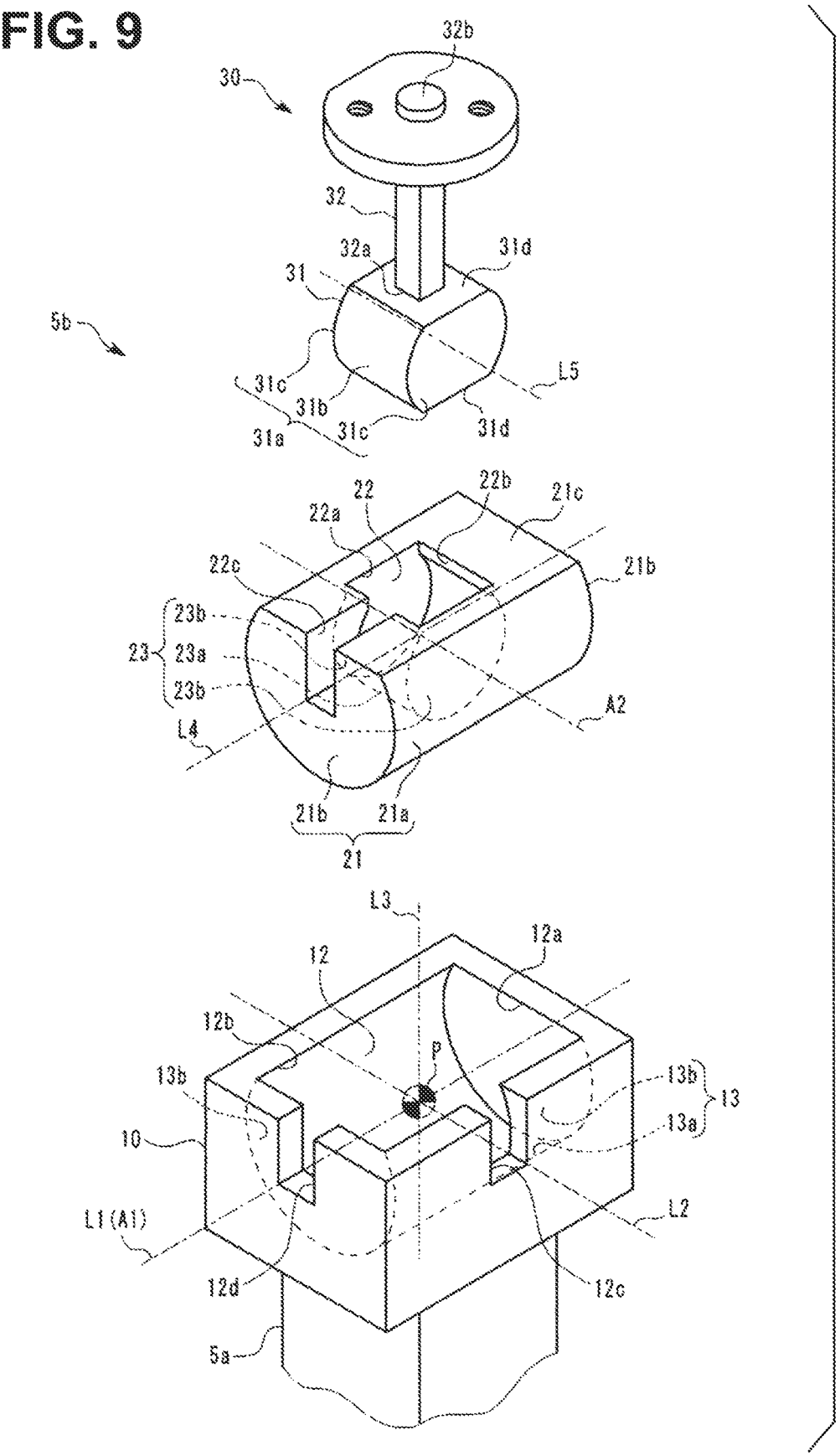
FIG. 9 is an exploded perspective view of a bearing portion of the second embodiment.
Figure 10:
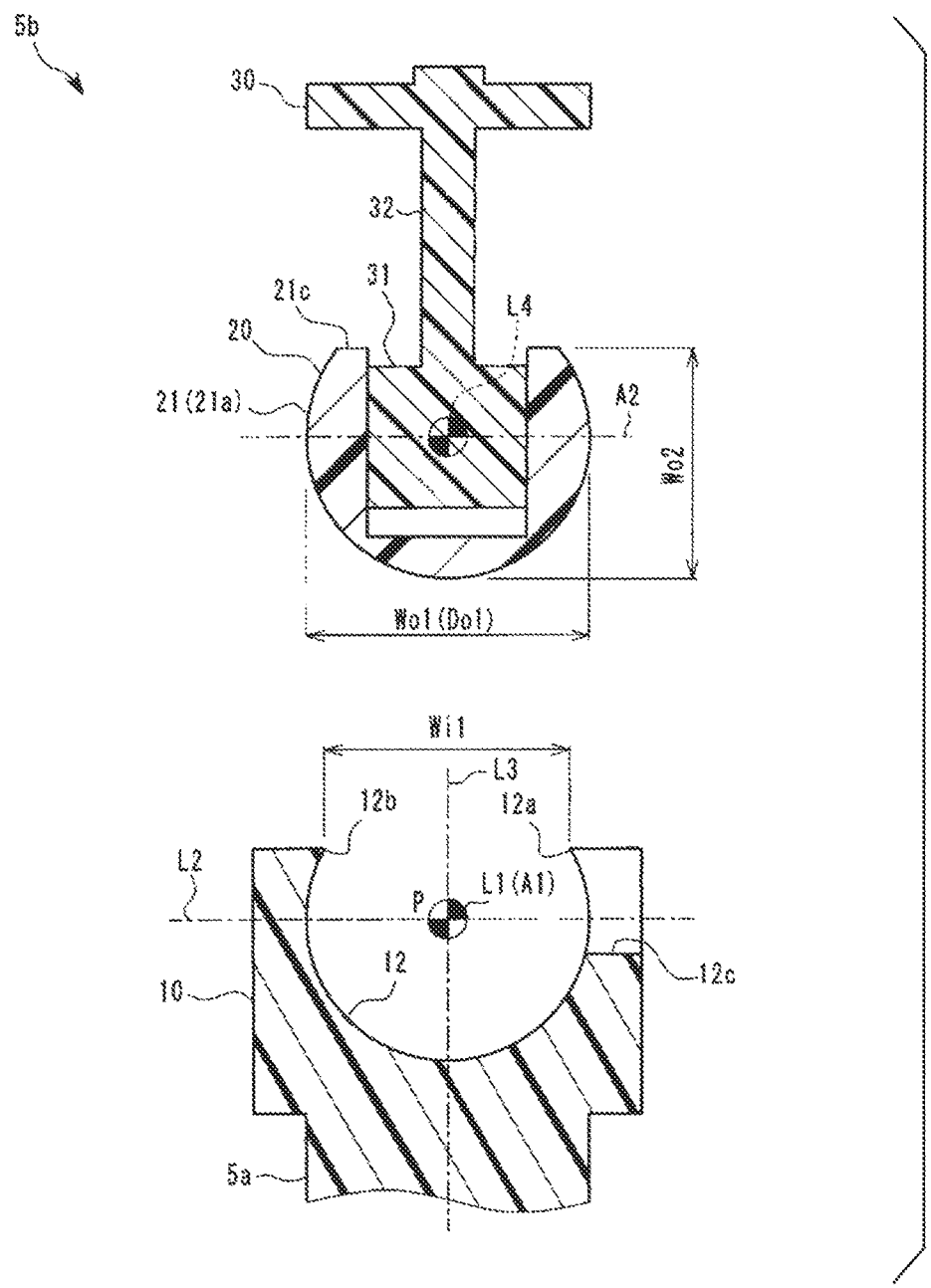
FIG. 10 is a sectional view of a first bearing and a second bearing of the second embodiment in a plane including a second linear axis and a third linear axis.
Figure 11:
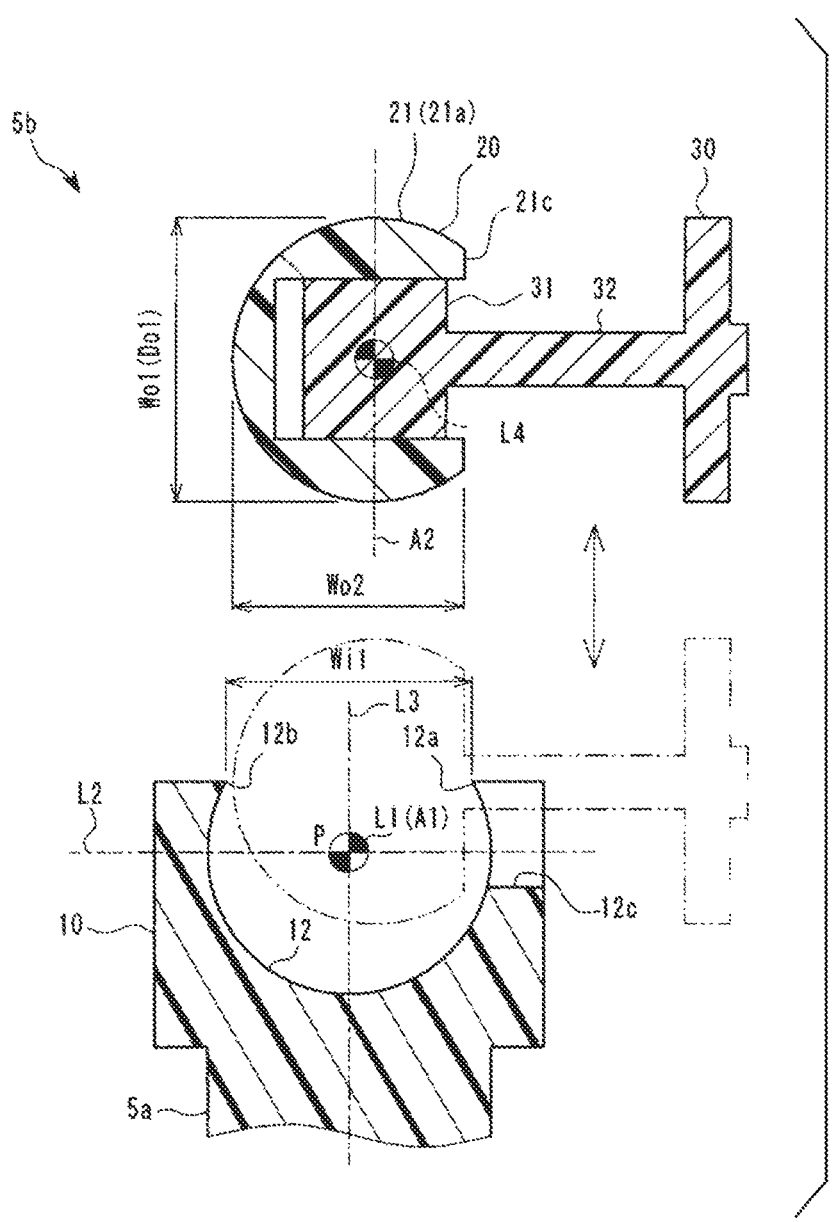
FIG. 11 is a view showing attachment/detachment of the first bearing and the second bearing in the second embodiment.
Figure 12:
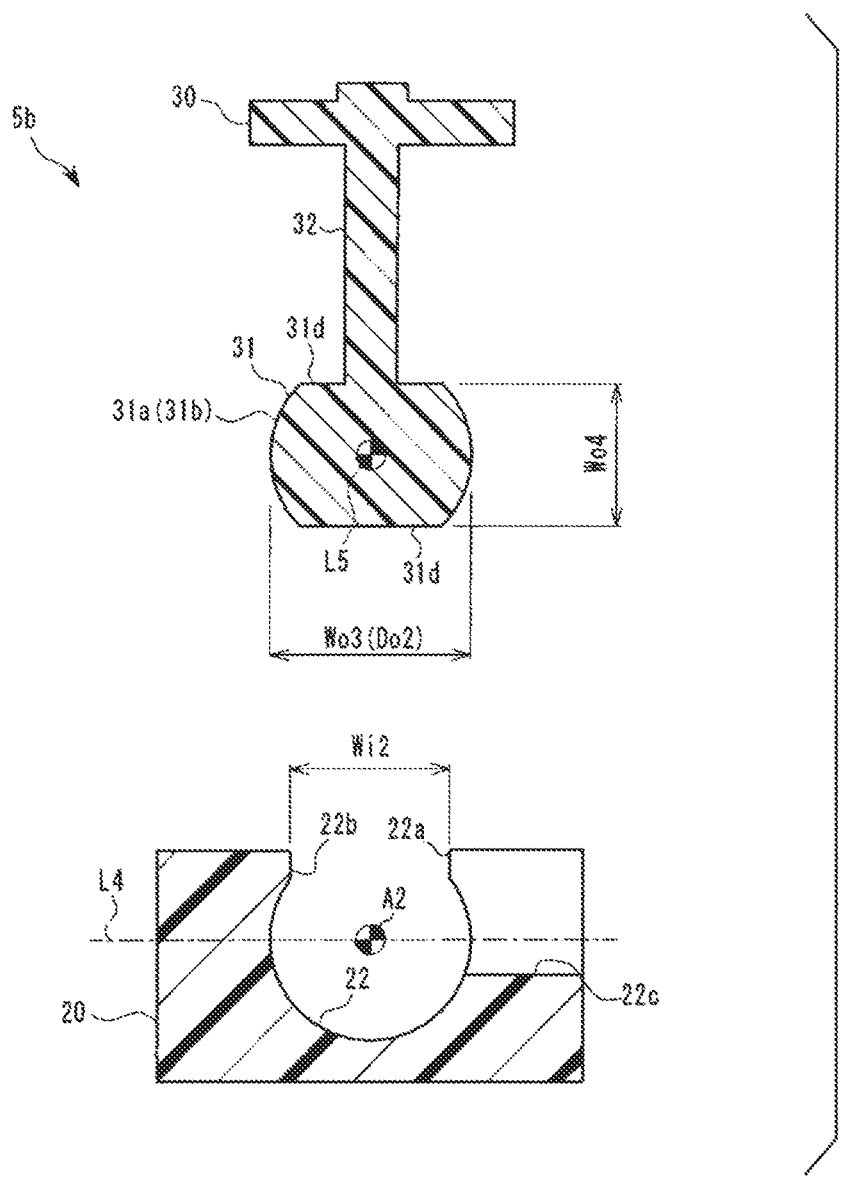
FIG. 12 is a sectional view of the second bearing and a shaft member in a plane including a first linear axis and the third linear axis in the second embodiment.
Figure 13:
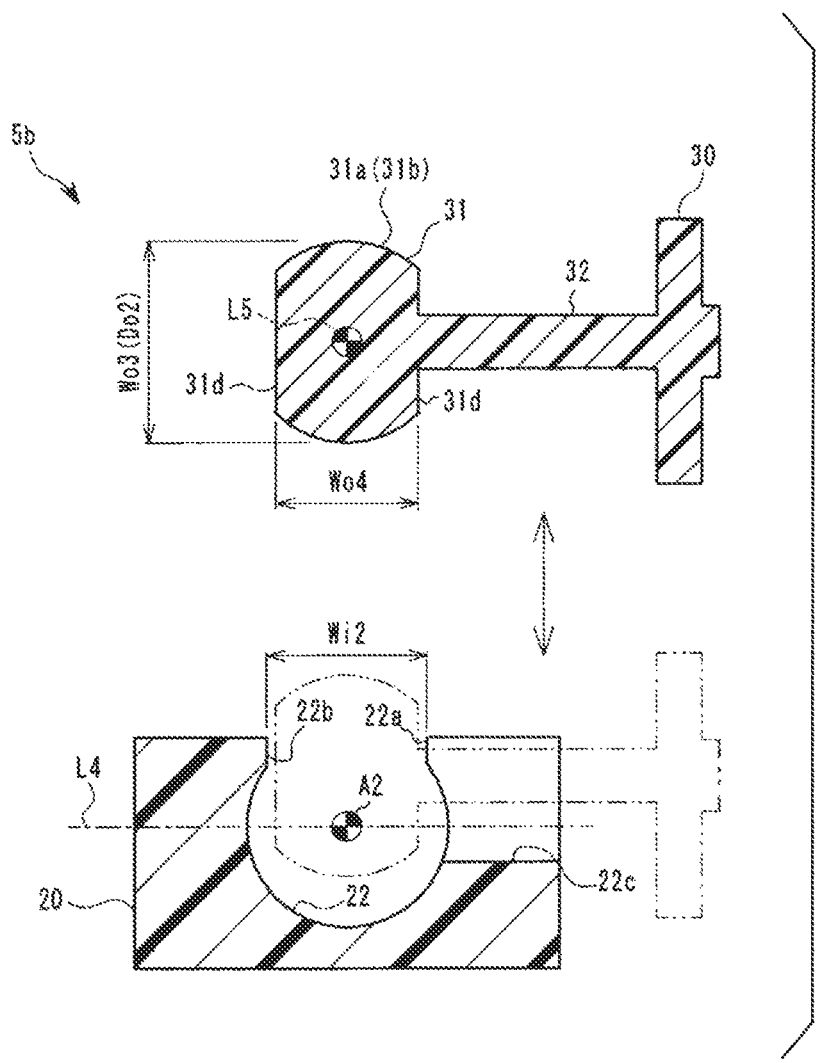
FIG. 13 is a view showing attachment/detachment of the second bearing and the shaft member in the second embodiment.

FIG. 8 is an exploded perspective view of the bending operation mechanism 5. FIG. 9 is an exploded perspective view of the bearing portion 5b. FIG. 10 is a cross-sectional view of the first bearing 10 and the second bearing 20 along the L2-L3 plane. FIG. 11 is a view showing attachment/detachment of the first bearing 10 and the second bearing 20. FIG. 12 is a cross-sectional view of the second bearing 20 and the shaft member 31 along the L1-L3 plane. FIG. 13 is a view showing attachment/detachment of the second bearing 20 and the shaft member 31.

The bending operation mechanism 5 of the present embodiment is different in configuration of the bearing portion 5b from the bending operation mechanism 5 in the first embodiment. The present invention is similar to the first embodiment in that the bearing portion 5b is configured of three members including the first bearing 10, the second bearing 20, and the shaft member 31, which can be manufactured by molding at low costs. The bearing portion 5b in the present embodiment has a configuration to prevent the second bearing 20 and the operation lever 30 from dropping off from the first bearing 10.

The first bearing 10 includes a first constriction portion 12b in the opening 12a of the first recess 12. The first constriction portion 12b is a through hole that communicates between the outside of the first bearing 10 and the inside of the first recess 12.

The first constriction portion 12b has an opening shape that interferes with a projected shape of the outline of the second bearing 20 on the L1-L2 plane when the second bearing 20 turns around the first central axis A1 in the range equal to or less than a prescribed angle θ3 from the neutral position. In other words, when an absolute value of the turning angle around the first central axis A1 from the neutral position is equal to or less than θ3, the second bearing 20 interferes with the first constriction portion 12b, so that the second bearing 20 cannot pass through the opening 12a of the first recess 12. Here, the prescribed angle θ3 is a value equal to or more than the first limit angle θ1.

The neutral position of the second bearing 20 at the time of turning around the first central axis A1 is the position where the opening direction of the second recess 22 coincides with the outward direction in the state where the fourth linear axis L4 of the second bearing 20 is parallel to the first central axis A1. In other words, even in the state where the second bearing 20 is positioned outside the first recess 12, the second bearing 20 can be located in the neutral position. The angle of turning of the second bearing 20 around the first central axis A1 from the neutral position is the angle formed between the opening direction of the second recess 22 and the outward direction, in the state where the fourth linear axis L4 of the second bearing 20 is parallel to the first central axis A1.

When the absolute value of the turning angle around the first central axis A1 from the neutral position is within the prescribed first angle range, which is larger than the prescribed angle θ3, a projected shape of the outline of the second bearing 20 on the L1-L2 plane has a shape that can pass through the first constriction portion 12b.

Specifically, the second bearing 20 in the present embodiment has one or two planar cut surfaces 21c formed on the cylindrical shape portion 21 which configures the outline.

The cut surface 21c is a flat surface which is separated by a prescribed distance from the second central axis A2 and which is parallel to the second central axis A2 and the fourth linear axis L4. The distance from the second central axis A2 to the cut surface 21c is less than the radius of the cylindrical surface 21a.

The cut surface 21c is formed on one of or both an area extending from the second central axis A2 to the side in the opening direction of the second recess 22 and an area extending from the second central axis A2 to the side in the depth direction of the second recess 22. In the present embodiment shown in the drawings, the cut surface 21c is formed only on one area that extends from the second central axis A2 to the side in the opening direction of the second recess 22.

Since the cut surface 21c is formed, the width of the outline of the second bearing 20 in the direction orthogonal to the second central axis A2 and the fourth linear axis L4 is smaller than the first outer diameter Do1 of the cylindrical surface 21a. Hereinafter, the width of the outline of the second bearing 20 in the direction parallel to the second central axis A2 is referred to as a first outline width Wo1. In the present embodiment, the first outline width Wo1 is equal to the first outer diameter Do1 of the cylindrical surface 21a. The width of the outline of the second bearing 20 in the direction orthogonal to the second central axis A2 and the fourth linear axis L4 is referred to as a second outline width Wo2. The second outline width Wo2 is the width of the outline of the second bearing 20 in the direction parallel to the third linear axis L3, in the state where the operation lever 30 is in the neutral position.

The first constriction portion 12b formed in the opening 12a of the first recess 12 in the first bearing 10 has a minimum opening width, which is a first opening width Wi1, in the direction parallel to the second linear axis L2. The first opening width Wi1 is smaller than the first outline width Wo1 of the second bearing 20 and larger than the second outline width Wo2.

As shown in FIG. 11, when the absolute value of the turning angle of the second bearing 20 around the first central axis A1 from the neutral position is in the vicinity of 90 degrees, the width of the outline of the second bearing 20 in the direction parallel to the second linear axis L2 is the second outline width Wo2. In this case, the second bearing 20 can pass through the first constriction portion 12b of the first recess 12.

Note that a lateral wall surface of the first recess 12 of the first bearing 10 has a first groove 12c formed to avoid interference with the operation lever 30 whose inclination angle around the first central axis A1 is in the vicinity of 90 degrees. The first groove 12c is shaped by notching the lateral wall surface of the first recess 12 with a prescribed width centered on the L2-L3 plane. The width of the first groove 12c is larger than the thickness of the lever member 32.

Since the first groove 12c is formed, it is possible to prevent interference between the lever member 32 and the lateral wall surface of the first recess 12, even in the state where the shaft member 31 is disposed in the second recess 22 of the second bearing 20.

Note that in the present embodiment shown in the drawings, the first groove 12c is formed only on one side with respect to the L1-L3 plane, though the first groove 12c may be formed on both the sides with respect to the L1-L3 plane.

On the other hand, as shown in FIG. 10, when the absolute value of the turning angle of the second bearing 20 around the first central axis A1 from the neutral position is equal to or less than the first limit angle θ1, the width of the outline of the second bearing 20 in the direction parallel to the second linear axis L2 is the first outline width Wo1. In this case, the second bearing 20 interferes with the first constriction portion 12b of the first recess 12, and therefore cannot pass through the first constriction portion 12b. Accordingly, in this case, the second bearing 20 is prevented from dropping off from the first recess 12.

The second bearing 20 includes a second constriction portion 22b in the opening 22a of the second recess 22. The second constriction portion 22*b* is a through hole that communicates between the outside of the second bearing 20 and the inside of the second recess 22.

The second constriction portion 22*b* has an opening shape that interferes with a projected shape of the outline of the shaft member 31 on an A2-L4 plane when the shaft member 31 turns around the second central axis A2 in the range equal to or less than a prescribed angle θ4 from the neutral position. In other words, when the absolute value of the turning angle of the shaft member 31 around the first central axis A1 from the neutral position is equal to or less than θ4, the shaft member 31 interferes with the second constriction portion 22*b*, so that the shaft member 31 cannot pass through the opening 22*a* of the second recess 22. Here, the prescribed angle θ4 is a value equal to or more than the second limit angle θ2.

The neutral position of the shaft member 31 at the time of turning around the second central axis A2 is the position where the longitudinal axis of the lever member 32 of the operation lever 30 is parallel to the opening direction of the second recess 22 of the second bearing 20, in the state where the fifth linear axis L5 of the shaft member 31 and the second central axis A2 are parallel. In other words, even in the state where the shaft member 31 is positioned outside the second recess 22, the shaft member 31 can be located in the neutral position. The turning angle of the shaft member 31 around the second central axis A2 from the neutral position is the angle formed between the longitudinal axis of the lever member 32 and the opening direction of the second recess 22, in the state where the fifth linear axis L5 of the shaft member 31 is parallel to the second central axis A2.

When the absolute value of the turning angle of the shaft member 31 around the second central axis A2 from the neutral position is within the prescribed second angle range, which is beyond the prescribed angle θ4, a projected shape of the outline of the shaft member 31 on the A2-L4 plane has a shape that can pass through the second constriction portion 22*b*.

The shaft member 31 in the present embodiment has one or two planar cut surfaces 31*d* formed on the cylindrical shape portion 31*a* which configures the outline.

The cut surface 31*d* is a flat surface which is separated by a prescribed distance from the fifth linear axis L5 and which is orthogonal to the longitudinal axis of the operation lever 30. The distance from the fifth linear axis L5 to the cut surface 31*d* is less than the radius of the cylindrical surface 31*b*.

The cut surface 31*d* is formed on one of or both an area extending from the fifth linear axis L5 to the side in a distal end direction of the operation lever 30 and an area extending from the fifth linear axis L5 to the side in a proximal end direction of the operation lever 30. In the present embodiment shown in the drawings, the cut surface 31*d* is formed in both the distal end direction and in the proximal end direction across the fifth linear axis L5.

Since the cut surfaces 31*d* are formed, the width of the outline of the shaft member 31 in the direction parallel to the longitudinal axis is smaller than the second outer diameter Do2 of the cylindrical surface 31*b*. Hereinafter, the width of the outline of the shaft member 31 in the direction orthogonal to the fifth linear axis L5 and the longitudinal axis is referred to as a third outline width Wo3. In the present embodiment, the third outline width Wo3 is equal to the second outer diameter Do2 of the cylindrical surface 31*b*. The width of the outline of the shaft member 31 in the direction parallel to the longitudinal axis is referred to as a fourth outline width Wo4. The fourth outline width Wo4 is the width of the outline of the shaft member 31 in the direction parallel to the third linear axis L3, in the state where the operation lever 30 is in the neutral position.

The second constriction portion 22*b* formed in the opening 22*a* of the second recess 22 in the second bearing 20 has a minimum opening width, which is a second opening width Wi2, in the direction parallel to the fourth linear axis L4. The second opening width Wi2 is smaller than the third outline width Wo3 of the shaft member 31 and larger than the fourth outline width Wo4.

As shown in FIG. 13, when the absolute value of the turning angle of the shaft member 31 around the second central axis A2 from the neutral position is in the vicinity of 90 degrees, the width of the outline of the shaft member 31 in the direction parallel to the fourth linear axis L4 is the fourth outline width Wo4. In this case, the shaft member 31 can pass through the second constriction portion 22*b* of the second recess 22.

Note that a lateral wall surface of the second recess 22 of the second bearing 20 has a second groove 22*c* formed to avoid interference with the operation lever 30 whose inclination angle around the second central axis A2 is the vicinity of 90 degrees. The second groove 22*c* is shaped by notching the lateral wall surface of the second recess 22 with a prescribed width centered on a plane which is orthogonal to the second central axis A2 and including the fourth linear axis L4. The width of the second groove 22*c* is larger than the thickness of the lever member 32.

Since the second groove 22*c* is formed, it is possible to prevent interference between the lever member 32 and the lateral wall surface of the second recess 22. The second groove 22*c* may also be formed on the opposite side from the second central axis A2.

In the present embodiment, a third groove 12*d* is formed on a lateral wall surface of the first recess 12 as shown in FIG. 9. The third groove 12*d* is formed to avoid interference with the operation lever 30 whose inclination angle around the second central axis A2 is in the vicinity of 90 degrees. Since the third groove 12*d* is formed in the first recess 12, it is possible to set the inclination angle of the operation lever 30 around the second central axis A2 to the vicinity of 90 degrees, even in the state where the second bearing 20 is disposed in the first recess 12.

On the other hand, as shown in FIG. 12, when the absolute value of the turning angle of the shaft member 31 around the second central axis A2 from the neutral position is equal to or less than the second limit angle θ2, the width of the outline of the shaft member 31 in the direction parallel to the fourth linear axis L4 is the third outline width Wo3. In this case, the shaft member 31 interferes with the second constriction portion 22*b* of the second recess 22, and therefore cannot pass through the second constriction portion 22*b*. Therefore, in this case, the shaft member 31 is prevented from dropping off from the second recess 22.

With the configuration described in the foregoing, the bearing portion 5*b* in the present embodiment prevents the second bearing 20 from dropping off from the first bearing 10 and prevents the operation lever 30 from dropping off from the second bearing 20.

The bearing portion 5*b* in the present embodiment can prevent separation of the first bearing 10, the second bearing 20, and the operation lever 30, after these members are assembled at the time of an assembling work of the endoscope 1. Therefore, the bending operation mechanism 5 for the endoscope 1 of the present embodiment can facilitate the assembling work of the bearing portion 5*b* into the cover member 3*a*.

Note that the bearing portion 5b in the present embodiment, as in the case of the first embodiment, is configured of three members including the first bearing 10, the second bearing 20, and the shaft member 31, each of which can be manufactured by molding at low costs. Since assembling of the bearing portion 5b is completed by simply combining the three members, the assembling is completed in a fewer procedures. Therefore, the bending operation mechanism 5 for the endoscope 1 in the present embodiment can be manufactured at low costs as in the case of the first embodiment.

Third Embodiment

Hereinafter, a third embodiment of the present invention will be described. In the following description, only the differences from the second embodiment will be described, and component members similar to the component members of the second embodiment will be designated by the same signs to omit the description as appropriate.

Figure 14:
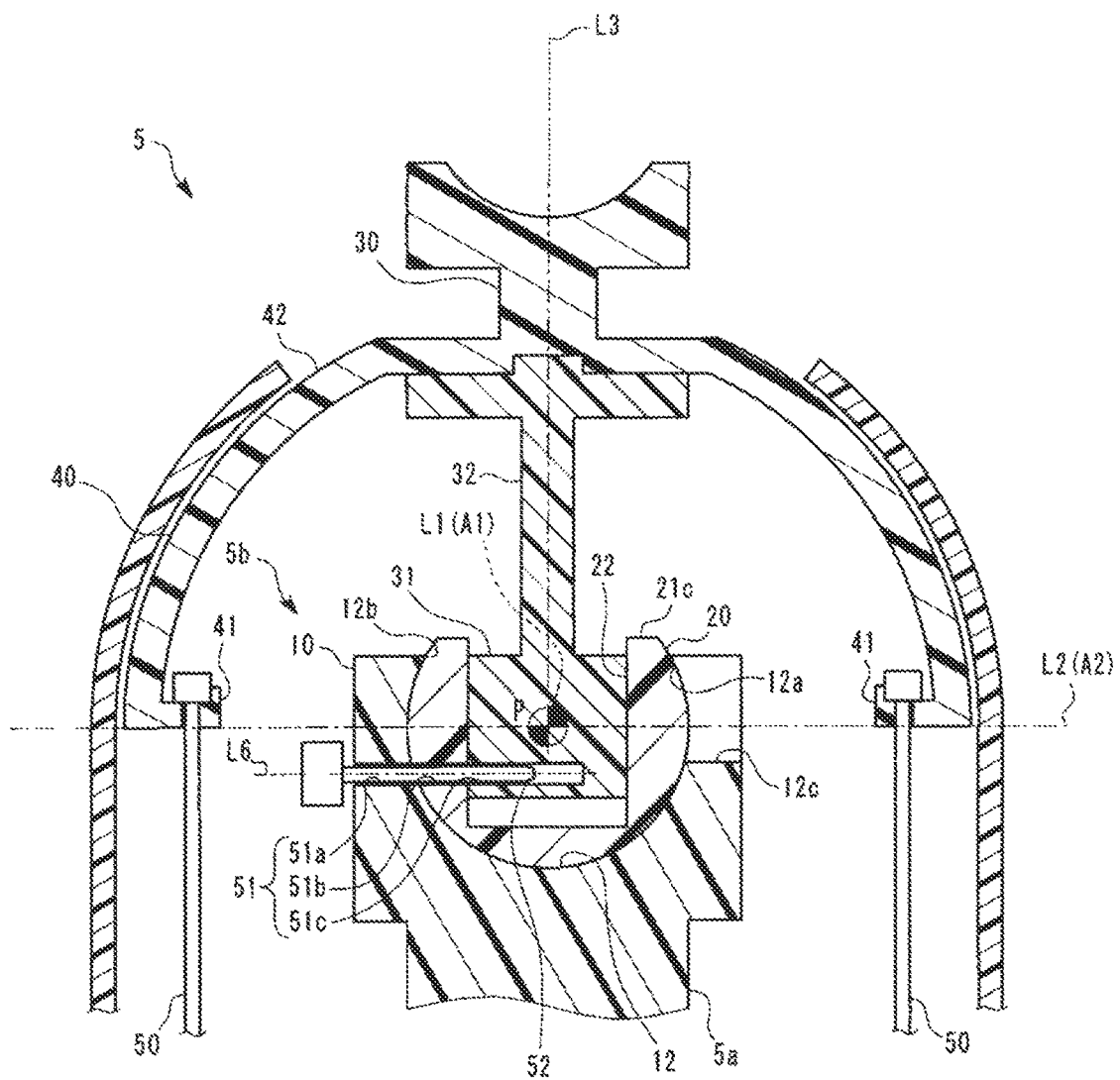
FIG. 14 is a sectional view of a bending operation mechanism of a third embodiment in a plane including a second linear axis and a third linear axis.

As shown in FIG. 14, the bending operation mechanism 5 of the present embodiment is different from the bending operation mechanism 5 of the second embodiment in that the bearing portion 5b includes holes 51.

The holes 51 are similar in configuration to the holes 51 in the first embodiment. In other words, the bearing portion 5b in the present embodiment includes one or more holes 51 having a depth to at least the shaft member 31 from the outer surface of the first bearing 10 in the state where the operation lever 30 is in the prescribed position.

Inside the hole 51, one pin 52 can be inserted as shown in FIG. 7, provided that the operation lever 30 is in the state of being at the prescribed position. The hole 51 is disposed so as to satisfy either the condition of not passing through the support point P or the condition of passing through the support point P but not in parallel with both the first central axis A1 and the second linear axis L2. Therefore, the pin 52 inserted in the hole 51 restricts the movement of the second bearing 20 and the shaft member 31 relative to the first bearing 10.

In the present embodiment, the operation lever 30 can be fixed in a prescribed position by inserting the pin 52 into the hole 51. For example, when the operation lever 30 can temporarily be fixed in the neutral position during assembling of the endoscope 1, it becomes possible to easily adjust the tension applied to the plurality of wires 50.

Therefore, since the bearing portion 51b in the present embodiment includes the holes 51, it becomes possible to facilitate an assembling work of the bending operation mechanism 5.

Other components of the bending operation mechanism 5 are similar to the components of the second embodiment. Therefore, the bending operation mechanism 5 of the present embodiment can prevent separation of the first bearing 10, the second bearing 20, and the operation lever 30, after these members are assembled at the time of an assembling work of the endoscope 1. Therefore, the bending operation mechanism 5 for the endoscope 1 of the present embodiment can facilitate the assembling work of the bearing portion 5b into the cover member 3a.

The bearing portion 5b in the present embodiment, as in the case of the first embodiment, is also configured of three members including the first bearing 10, the second bearing 20, and the shaft member 31, each of which can be manufactured by molding at low costs. Since assembling of the bearing portion 5b is completed by simply combining the three members, the assembling is completed in a fewer procedures. Therefore, the bending operation mechanism 5 for the endoscope 1 in the present embodiment can be manufactured at low costs as in the case of the first embodiment.

The present invention is not limited to the embodiments disclosed. Changes are possible as appropriate without departing from the gist or idea of the present invention which are understood from the claims and the specification in its entirety. Endoscopes with such changes are also included in the technical scope of the present invention.

What is claimed is:

1. An endoscope, comprising: a first bearing including a first recess, the first recess having a first interior cylindrical shape with a first axis;
   a second bearing having a first exterior cylindrical shape corresponding to the first interior cylindrical shape such that the second bearing is retained rotatably in the first recess to rotate around the first axis, the second bearing including a second recess, the second recess having a second interior cylindrical shape with a second axis intersecting the first axis; and
   an operation lever including a first shaft having a second exterior cylindrical shape corresponding to the second interior cylindrical shape such that the first shaft is retained rotatably in the second recess to rotate around the second axis
   wherein the operation lever includes a second shaft extending from an outer surface of the first shaft in a direction orthogonal to the second axis, the second shaft configured to rotate together with the first shaft, and
   the first bearing further includes a first groove in communication with the first recess, the first groove configured to receive a portion of the second shaft when the second shaft is rotated about the first axis to be within the first groove.

2. The endoscope according to claim 1, further comprising a stopper configured to restrict movement of the operation lever in a longitudinal axis direction of the operation lever.

3. The endoscope according to claim 2, wherein
   the stopper is a pin,
   the first bearing, the second bearing, and the first shaft include respective holes that simultaneously accept the pin, and
   when the pin is inserted into the holes, movement of the first bearing, the second bearing, and the operation lever is restricted.

4. The endoscope according to claim 3, wherein the holes are formed at a position apart from the first axis and apart from the second axis.

5. The endoscope according to claim 1, wherein
   the first recess is open in a longitudinal axis direction of the operation lever,
   the second recess is open in a direction orthogonal to the first axis and the second axis.

6. The endoscope according to claim 1, wherein
   the first shaft having:
   a largest first width in a first direction orthogonal to a longitudinal axis direction of the operation lever; and
   a largest second width in a second direction orthogonal to the first direction; and
   a minimum width of an opening of the second recess is smaller than the largest first width and larger than the largest second width.

7. The endoscope according to claim 1, wherein
the operation lever includes a second shaft extending from an outer surface of the first shaft in a direction orthogonal to the second axis, the second shaft configured to rotate together with the first shaft, and
the endoscope further includes a second groove in communication with the second recess, the second groove configured to receive a portion of the second shaft when the second shaft is rotated about the second axis to be within the second groove.

8. The endoscope according to claim 1, further comprising a stopper, the stopper is a cover member having an opening configured to restrict movement of the operation lever about the first axis and about the second axis.

9. The endoscope according to claim 8, wherein the operation lever extends to an outside of the cover from the opening.

10. The endoscope according to claim 1, further comprising a finger contact member disposed at an end portion of the operation lever.

11. The endoscope according to claim 1, further comprising:
an operation portion; and
an insertion portion disposed distally relative to the operation portion, the insertion portion including a bending portion,
wherein the operation lever is disposed in the operation portion and connected to a plurality of wires configured to bend the bending portion.

12. The endoscope according to claim 11, wherein the operation lever is provided with a dome body, a proximal end of each of the plurality of wires is fixed to the dome body.

13. The endoscope according to claim 12, wherein the dome body further comprising a retention member to which the plurality of wires are fixed.

14. A bending operation mechanism for use with an endoscope, the bending operation mechanism comprising:
a first bearing including a first recess, the first recess having a first interior cylindrical shape with a first axis;
a second bearing, the second bearing having a first exterior cylindrical shape corresponding to the first interior cylindrical shape such that the second bearing is retained rotatably in the first recess to rotate around the first axis, the second bearing including a second recess, the second recess having a second interior cylindrical shape with a second axis intersecting the first axis; and
an operation lever including a first shaft having a second exterior cylindrical shape corresponding to the second interior cylindrical shape such that the first shaft is retained rotatably in the second recess to rotate around the second axis intersecting the first axis;
wherein the operation lever includes a second shaft extending from an outer surface of the first shaft in a direction orthogonal to the second axis, the second shaft configured to rotate together with the first shaft, and
the first bearing further includes a first groove in communication with the first recess, the first groove configured to receive a portion of the second shaft when the second shaft is rotated about the first axis to be within the first groove.

15. An operation portion for an endoscope, the operation portion comprising the bending operation mechanism according to claim 14.

16. The endoscope according to claim 1, wherein the second bearing having:
a largest first width in a first direction orthogonal to an opening direction of the second recess; and
a largest second width in a second direction orthogonal to the first direction, the largest second width being smaller than the largest first width, and
a minimum width of the opening of the first recess is smaller than the largest first width and larger than the largest second width.

17. The endoscope according to claim 1, further comprising converting means for converting movement of the operation lever to bending of a bending section at a distal portion of the endoscope.

18. The endoscope according to claim 1, wherein the converting means comprising a plurality of wires operatively connected at one end to the operation lever and at another end to the bending section.

19. The endoscope according to claim 1, wherein first axis and the second axis intersect at 90 degrees.

* * * * *